US011468988B1

(12) United States Patent
Wang et al.

(10) Patent No.: US 11,468,988 B1
(45) Date of Patent: Oct. 11, 2022

(54) FACILITATING REMOTE CONTROL OF OXYGEN SUPPLY

(71) Applicant: Telesair, Inc., Irvine, CA (US)

(72) Inventors: Qing Wang, Irvine, CA (US); Andrew Hull, Irvine, CA (US)

(73) Assignee: TELESAIR, INC., Irvine, CA (US)

( * ) Notice: Subject to any disclaimer, the term of this patent is extended or adjusted under 35 U.S.C. 154(b) by 0 days.

(21) Appl. No.: 17/569,528

(22) Filed: Jan. 6, 2022

(51) Int. Cl.
 *G16H 40/67* (2018.01)
 *G16H 40/63* (2018.01)
 *A61M 16/06* (2006.01)

(52) U.S. Cl.
 CPC ........ *G16H 40/67* (2018.01); *A61M 16/0672* (2014.02); *G16H 40/63* (2018.01); *A61M 2205/3368* (2013.01); *A61M 2205/3553* (2013.01); *A61M 2205/3561* (2013.01)

(58) Field of Classification Search
 CPC .......... G06F 21/32; G06F 21/31; G06F 21/35; G06F 21/44; G06F 21/6245; A61M 16/00; A61M 16/024; A61M 16/0051; A61M 16/101; A61M 16/10; A61B 5/02055; A61B 5/0205; A61B 5/0022; A61B 5/14551; A61B 5/14532; G16H 40/67; G16H 40/63; G16H 10/60; G16H 20/13; A24F 47/008; H04L 63/0861; H04L 63/10; H04W 12/08
 See application file for complete search history.

(56) References Cited

U.S. PATENT DOCUMENTS

2022/0046208 A1* 2/2022 Kannan ............... H04L 65/1069
2022/0072321 A1* 3/2022 O'Connor ............. G16H 20/30

OTHER PUBLICATIONS

IoT in Patient Respiratory Condition & Oxygen Regulator's Flowrate Monitor, Puspitasari et al., Proc. EECSI 2020—Oct. 1-2, 2020. (Year: 2020).*

* cited by examiner

*Primary Examiner* — Manuel A Mendez
(74) *Attorney, Agent, or Firm* — Javalon Law, PC

(57) ABSTRACT

Embodiments provide an oxygen supply device having multiple operational states including a first state and a second state. In the first state, the oxygen supply device is controllable to a local control instruction such that the oxygen supply device can be operated by a user physically located within a proximity of the oxygen supply device. In the second state, the oxygen supply device is only controllable to a remote-control instruction such that the oxygen supply device can be operated by a user remote to the oxygen supply device. For example, the user can be located in an office remote to a location of the oxygen supply device, which, for example, may be placed at a patient's home. In the second state, the user is enabled to control the oxygen supply device from a device associated with the user in the remote location.

20 Claims, 7 Drawing Sheets

FACILITATING REMOTE CONTROL OF OXYGEN SUPPLY

FIELD OF THE INVENTION

The present disclosure relates to mode of operations of an oxygen supply device and more particular to remote-control of the oxygen supply device.

BACKGROUND OF THE INVENTION

A control system is a system of devices which manages, commands, directs, or regulates behavior of one or more end devices or end systems. A control system uses its computing capability to produce desired outputs for controlling one or more end devices or end systems. Examples of control system can range from a single home heating controller using a thermostat controlling a domestic boiler to large industrial control systems which are used for controlling processes or machines.

An oxygen supply device is a device that supplies an oxygen-enriched product gas stream. An oxygen supply device can be used in health care institutions to supply oxygen to patients for treatment of breathing-related disorders such as asthma, pneumonia, respiratory distress syndrome, bronchopulmonary dysplasia, chronic obstructive pulmonary disease.

High Flow Nasal Cannula (HFNC) is one kind of oxygen supply device providing oxygen therapy to respiratory function comprised patients and is recommended by the World Health Organization (WHO) and US National Institutes of Health (NIH) as the first device to treat COVID-19 patients. SARS-CoV-2 virus which causes highly contagious COVID-19. Operating HFNC for COVID-19 patients creates enormous risk to health care workers. Over 38,000 healthcare workers were infected by SARA-VoV-2 in Los Angeles hospitals alone. Novel embodiments of interactive remote communication and remote-control are presented for treating highly contagious diseases and protecting nursers, respiratory therapists, and physicians. Another major benefit of a remote high flow nasal cannula is that it brings healthcare level of developing or undeveloped areas to advanced healthcare level. It eliminates the need to change Personal Protective Equipment (PPE) and saves not only resources but more importantly, healthcare workers time for changing PPE, giving them more time to care their patients.

SUMMARY OF THE INVENTION

Various embodiments provide a solution to protect our healthcare workers in COVID-19 and future pandemic. The systems and methods presented to treat COVID-19 patients and protect our healthcare workers can also be used in treating other infectious diseases and future diseases. In accordance with the present disclosure, embodiments provide an oxygen supply device having multiple operational states including a first state and a second state. In the first state, the oxygen supply device is controllable to a local control instruction such that the oxygen supply device can be operated by a user physically located within a proximity of the oxygen supply device. In the second state, the oxygen supply device is only controllable to a remote-control instruction such that the oxygen supply device can be operated by a user remote to the oxygen supply device. For example, the user can be in an office remote to a location of the oxygen supply device, which, for example, may be placed at a patient's home. In the second state, the user is enabled to control the oxygen supply device from a device associated with the user in the remote location.

In some embodiments, the oxygen supply device in accordance with the disclosure is configured with an element that can authenticate a user so that the user can control the oxygen supply device in the first state. In some embodiments, the oxygen supply device in accordance with the present disclosure is configured with logic that can receive and accept a request from a remote computing device requesting control of the oxygen supply device in the second state. In those embodiments, the logic can determine whether a switch from the first state to the second state and vice versa is permitted to be carried out.

In some embodiments, a personal assistant device (PDA) is provided to a patient using the oxygen supply device in accordance with the present disclosure. In those embodiments, the PDA provided to the patient is configured to facilitate the patient to request an adjustment of one or more settings of the oxygen supply device, and/or a local control of the oxygen supply device.

In some embodiments, a PDA is provided to a health care worker. In those embodiments, the PDA provided to the health care worker is configured to implement an interface that can generate one or more alerts about the patient's condition(s) using the oxygen supply device in accordance with the present disclosure. In those embodiments, the PDA provided to the health care worker is configured to provide one or more physiological parameters about the patients to help the health care worker determine whether setting adjustment is needed for the oxygen supply device while supplying oxygen to the patient.

Other objects and advantages of the invention will be apparent to those skilled in the art based on the following drawings and detailed description.

DETAILED DESCRIPTION

Figure 1:
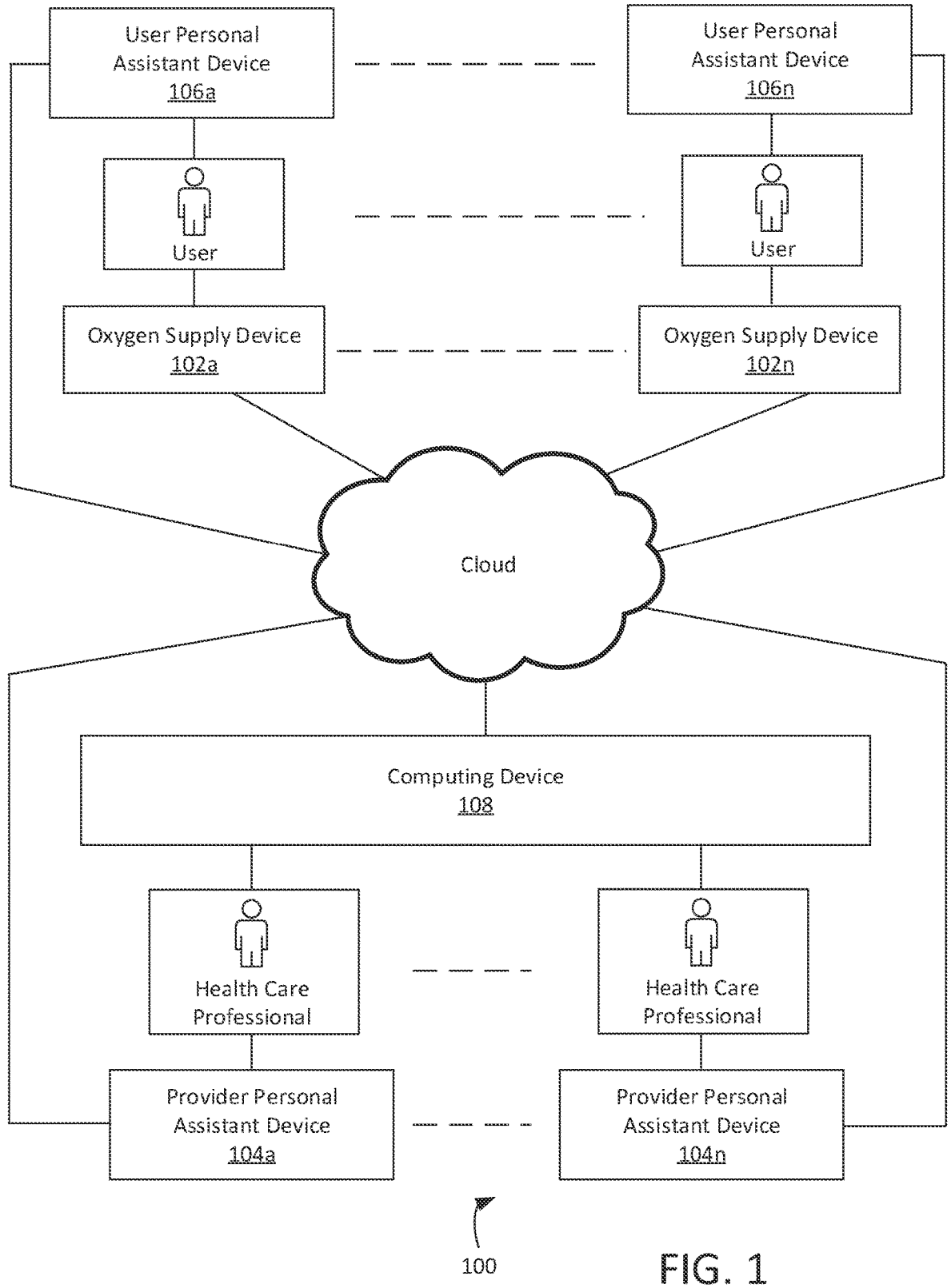
FIG. 1 illustrates an example environment in which the oxygen supply device in accordance with the present disclosure is applied.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed. For a particular repeated reference numeral, cross-reference may be made for its structure and/or function described and illustrated herein.

Patients with moderate to severe COVID-19 are often present with pneumonia that could lead to hypoxemia. High flow nasal cannula (HFNC) is recommended by the World Health Organization (WHO) and National Institutes of Health (NIH) as a way to provide supplemental oxygen for COVID-19 patients who are hypoxemic. HFNC can provide humidified and body-temperature oxygen from 10 to-80 L/min to meet patients' demand, and decrease patients' discomfort and work of breathing, whereas 10-80 L/min is the flow range in liter per minute (L/min). The upper end of the range, e.g., 80 L/min can be set to a lower limit for certain patients, such as 40 L/min for pediatric patients, or to a higher limit for, such as 100 L/min for special patient need. This upper limit can be a programmable configuration and set before the device is shipped to a customer, or set by a healthcare worker according to patient's condition. The upper limit is implemented to protect patient in case of device malfunction or in unintended risk setting. It also improves ventilation and oxygenation through the washout of nasopharyngeal dead space. When being compared to conventional oxygen therapy or Noninvasive Positive Pressure Ventilation (NIPPV), HFNC has been demonstrated to decrease 90-day mortality and intubation rate for patients with acute hypoxemic respiratory failure.

As patient's condition changes with time, the settings of HFNC also need to be adjusted accordingly. However, the state-of-the-art HFNC operates like a standalone device, with no connectivity and integration with other hospital systems or devices; therefore, it requires health care workers (HCWs) to be within close proximity of patients whenever the adjustments of the settings are needed.

Due to the nature of high gas flow, both the WHO and NIH categorized HFNC as an aerosol generating procedure that is defined as a high-risk exposure for HCWs when used on a COVID-19 patient; it becomes a critical battlefront to ensure the safety of HCWs. Studies have shown that frontline HCWs are at least 3 times more likely to be infected. The danger to HCWs is worse when we have limited supplies of PPE. Compared with the HCWs who do not have exposure to patients with COVID-19, HCWs who have inadequate or reused PPE with exposure to patients with COVID-19 have 5-6 times higher infection rate in Los Angeles County, the most populous county in the United states, over 38,000 HCWs and first responders have been confirmed with COVID-19 as of March 2021. COVID-19 pandemic has been a tremendous challenge to our societies as a whole, but hospitals and our frontline HCWs have been under unprecedented stress because of the overwhelming number of COVID-patients and highly contagious nature of COVID-19.

During COVID-19 pandemic, different waves of infection in different countries have been happening in different time. With remote monitor and remote-control, healthcare workers in countries or areas with lower infections can help countries and areas with higher infections. Remote high flow nasal cannula also provides healthcare workers in areas with advanced healthcare to help respiratory compromised patients in underdeveloped areas and countries.

Another issue with application of the state-of-the-art oxygen supply device is that it cannot make timely adjustment of its configurations in response to patient's physiological parameter changes even when the patient is at health care institution. For example, when a physiological parameter of a patient changes, the state-of-the-art oxygen supply device can only be adjusted when a health care provider comes to the patient's site through a periodical check or for an alarm event. When an alarm event is processed, a respiratory therapist or a physician is noticed. The respiratory therapist or the physician then needs to walk to the patient's site to evaluate the patient and make necessary adjustment of the oxygen supply device.

Yet another issue with the state-of-the-art oxygen supply device is that it is not practical for home use. The largest patient population for oxygen supply device such as HFNC is at home Chronic Obstructive Pulmonary Disease (COPD) patients. Clinical studies have shown that using HFNC at home can reduce exacerbation, hospital admissions, and symptoms in COPD patients with hypoxic failure. Yet it is not practical to have healthcare providers stay with COPD patients at their home all time to make such necessary adjustment.

Various embodiments provide a solution to protect our healthcare workers in COVID-19 and future pandemic. The system and methods presented to treat COVID-19 patients and protect our healthcare workers can also be used in treating other infectious diseases and the treatment of future diseases.

In accordance with the present disclosure, embodiments provide an oxygen supply device having multiple operational states including a first state and a second state. In the first state, the oxygen supply device is controllable to a local control instruction such that the oxygen supply device can be operated by a user physically located within a proximity of the oxygen supply device. In the second state, the oxygen supply device is only controllable to a remote-control instruction such that the oxygen supply device can be operated by a user remote to the oxygen supply device. For example, the user can be located in an office remote to a location of the oxygen supply device, which, for example, may be placed at a patient's home. In the second state, the user is enabled to control the oxygen supply device from a device associated with the user in the remote location.

By way of illustration, thus not intended to be limiting, in various embodiments, the user is a nurse responsible for monitoring a COVID patient on an oxygen supply device at the patient's home. The nurse does not necessarily have to be present in the patient's home to control the oxygen supply device. In accordance with the present disclosure, the nurse can be located remotely, for example at the nurse's hospital, clinic or his/her home, to control the oxygen supply device based on patient's condition reported to the nurse. For example, the nurse may be receiving patient's vital signs such as breathing rate on a device associated with the nurse. In that example, the nurse is enabled to adjust an oxygen flow rate on the oxygen supply device remotely through a computing device if the patient's breathing and other vital signs indicate that the patient is undergoing a breathing difficulty. In this way, the nurse need not be present at patient's site and thus risk of infection for the nurse is eliminated and management efficiency is also improved for the nurse.

A few challenges however may be present when providing such remote-control of an oxygen supply device to the nurse in the example given above. For example, safety is an issue when the oxygen supply device is not monitored or controlled in a professional setting—for instance at the hospital where the nurse is located. For instance, when the oxygen supply device is left in the patient's home, there is risk that the oxygen supply device may be used in a way not in compliance with safety protocol for operating the oxygen supply device. As mentioned above, oxygen supply device such as HFNC is typically controlled by a professional in a hospital setting so that the patient or patient's visitors (such as family members of the patient) may not adjust the oxygen supply device.

However, traditional oxygen supply device such as an HFNC is not configured or designed in a way to allow the HFNC to be left in patient's home free from the risk of it being mistakenly used by someone. That is, safety measures should be adopted in providing remote-control of oxygen supply device.

For addressing the aforementioned safety concerns, in various embodiments, the oxygen supply device in accordance with the present disclosure is not controllable locally by someone when the oxygen supply device is in a remote working state. In those embodiments, a switch request is needed to allow a local control of the oxygen supply device. In those embodiments, the switch request has to be made by an authorized user of the oxygen supply device; and only after an authorization is verified is the request granted. In various embodiments, a switch request is a straight forward switch state request or is a command, such as changing a setting or configuration of the oxygen supply device.

Another challenge in providing the remote-control of an oxygen supply device in accordance with the present disclosure is privacy issue. Health data about the patient is communicated from the oxygen supply device to a remote site where an authorized user of the oxygen supply device is located. Thus, care should be taken to ensure such data is safe and will not be compromised.

For addressing this, various embodiments provide encryption methods to encrypt health data of the patient to prevent privacy breach during the aforementioned communication. In those embodiments, health information regarding the patient is processed at the oxygen supply device before it is communicated remotely to a computing device associated with an authorized user of the oxygen supply device such as a nurse.

Still another challenge in providing remote-control of the oxygen supply device is risk of remote-control instructions are hacked by a malicious actor to cause safety intrusion to the patient. For example, an oxygen flow rate adjustment instruction may be preposterously issued by a hacker to jeopardize the patient's health. For addressing this, in various embodiments, an oxygen supply device in accordance with the disclosure is configured to verify whether an incoming remote-control instruction is from an authorized user. In an event that the control instruction is not verified as being from the authorized user, the remote-control instruction is ignored by the oxygen supply device.

Among other benefits, various embodiments do not require health care providers to be within close proximity of patients to adjust configurations of the oxygen supply device when needed. In those embodiments, multiple health care providers can remotely control the oxygen supply device without physically touching the device. This allows health care providers to make timely adjustment of the oxygen supply device in response to patients' physiological parameter changes, thus improving time efficiency of the oxygen supply device.

Another motivation behind the present disclosure is to provide a safe environment for health care providers in oxygen supply device applications. The environment presented in the present disclosure allows health care providers to avoid being physically present in an aerosol generating procedure when treating patients with severe respiratory distress. With such an environment, health care providers can reduce infection risks by configuring the oxygen supply device remotely from a different space. In this way, the environment allows patients and health care providers to use the oxygen supply device for home-use applications.

In some embodiments, as mentioned, the oxygen supply device includes multiple operational states including a first operational state and a second operational state. In various embodiments, the oxygen supply device is configured to receive a switch request requesting to switch the oxygen device from the second operational state to the first operational state.

The switch request may be made by a healthcare provider. In some embodiments, a personal digital assistant (PDA) device is provided to the health care provider to enable the health care provider to initiate the switch request from the PDA. In those embodiments, the PDA is connected to the oxygen supply device through wireless communication channels.

Attention is now directed to FIG. 1, where an example environment 100 in which the oxygen supply device in accordance with the present disclosure is applied. As shown in this example, the environment 100 includes multiple oxygen supply devices 102, such as devices 102a and 102n shown in this example. As shown, an individual oxygen supply device, such as 102a, is associated with a corresponding user (for example, a patient). As also shown, an individual user in the environment 100 is associated with a PDA, such as a PDA 106a and 106n. As mentioned, an example of a PDA in accordance with the present disclosure may be a smart device (for example a smart phone).

As still shown in FIG. 1, individual oxygen supply devices are operatively connected to a computing device 108 via a cloud. By way of non-limiting example, the computing device 108 may be a computer server or a workstation provided by a hospital. Cloud may be a server in a closed network environment. As shown, the computing device 108 is associated with multiple health care providers, such as nurse, doctor, respiratory therapist and/or any other health care provider. It should be understood, although a cloud is shown in this example as a communication medium to connect the oxygen supply devices and the computing device 108, this is not intended to be limiting. It is contemplated that the oxygen supply devices in accordance with the present disclosure can be connected to the computing device 108 using some other communication medium, for example through a P2P network, a mesh network and/or any other type of private or public computer networks.

As also shown, an individual health care provider in the environment 100 is associated with a PDA, such as PDA 104a and 104n shown in this example. By way of illustration, thus not intended to be limiting, an example scenario of applying the oxygen supply device 102a is described. In this scenario, the oxygen device 102a is located in the home of the user associated with the oxygen supply device 102a. In this scenario, the oxygen supply device 102a is controlled remotely by a nurse through the computing device 108 located in a hospital. Control instructions are generated by the nurse via the computing device 108a and transmitted to the oxygen supply device 102a. For example the control instructions can include an instruction to control an oxygen flow rate of the oxygen supply device 102 when supplying oxygen to the user.

In this scenario, the nurse can receive various vital signs about the user on the PDA 104a so that the nurse may generate the aforementioned control instructions to control the oxygen supply device 102a remotely in response to the vital signs about the user. For example, the nurse may generate a control instruction to increase an oxygen flow rate on the oxygen supply device 102a when supplying oxygen to the user in response to a breathing difficulty being observed by the nurse on the PDA 104a.

In this scenario, the user is enabled to generate a request to the nurse using the PDA 106a. The request may ask the nurse to increase the oxygen flow rate on the oxygen supply device 102a. In this way, the nurse may issue a control instruction accordingly in response to the user's request. The user request may be received on the computing device 108 or may be received on the PDA 104a associated with the nurse in this scenario.

Figure 2:
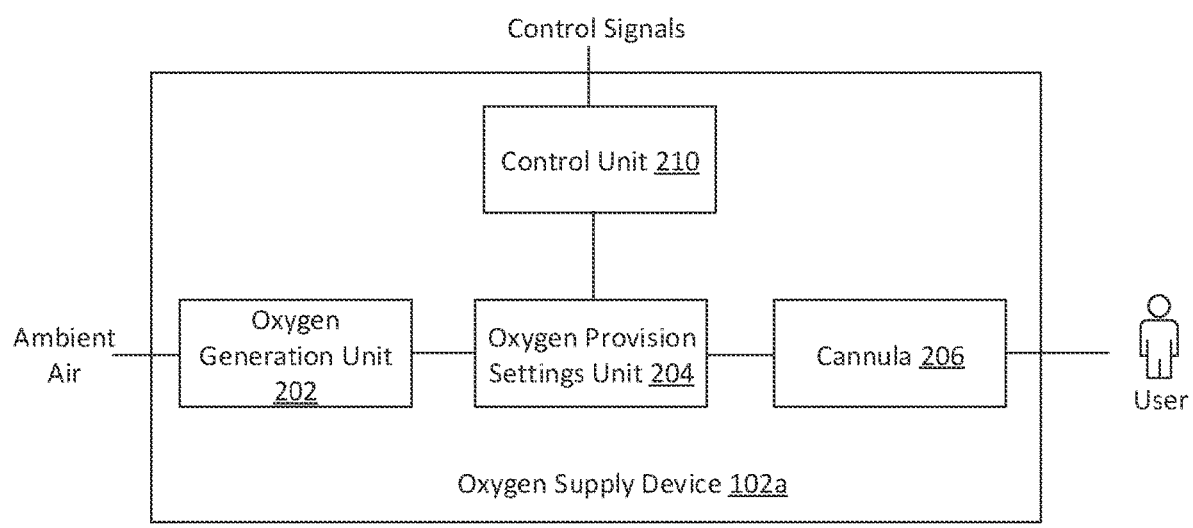
FIG. 2, illustrates an example an oxygen supply device shown in FIG. 1.

With an example environment where the oxygen supply device in accordance with the disclosure has been generally described, attention is now directed to FIG. 2, which illustrates an example an oxygen supply device 102a shown in FIG. 1.

In this example, the oxygen supply device 102a includes an oxygen generation unit 202, an oxygen provision settings unit 204, one or more of a cannula 206, a control unit 208, and/or any other units. The oxygen generation unit 202, in this example, is configured to receive ambient air and generate oxygen by separating the oxygen from the ambient air. The oxygen provision settings unit 204, in this example, is configured to provide the oxygen generated by the oxygen generation unit 202 to the user via the cannula 206 in accordance with one or more settings. For example, the settings may include oxygen purity, oxygen flow rate per second, oxygen density, oxygen provision cycle time, and/or any other settings. The cannula 206 may include a component that may be attached to the user to deliver the oxygen to the user in accordance with the oxygen provision controlled by the oxygen provision settings unit 204.

The control unit 210, in this example, is configured to receive a control signal indicating a control instruction for execution by the control unit 210. As mentioned, the control signal can indicate a control instruction to adjust one or more settings through the oxygen provision settings unit 204. As also mentioned, there can be at least two sources of the control signal—local and remote. For ease of description herein, a control signal provided through the oxygen supply device is referred to as a local control signal and a control signal provided remotely through a cloud (such as the cloud shown in FIG. 1) is referred to as a remote-control signal. As also mentioned, a novelty of the oxygen supply device shown in FIG. 2 is that it is controllable to a remote-control signal.

In general, at least two types of control signals (whether local or remote) can be received by the control unit 210. The first type is for controlling an operation of the oxygen supply device. For example, a control signal indicates to the oxygen supply device to adjust its oxygen flow rate through the oxygen provision settings unit 204. The second type is for switching working states of the oxygen supply device. In accordance with the present disclosure, the oxygen supply device shown in FIG. 2 has at least two working states, including a first working state and a second working state.

In the first working state, the oxygen supply device is controllable to a local control instruction and in the second working state, the oxygen supply device is controllable only to a remote-control instruction. For ease of description, not intended to be limiting, the first working state is referred to as a local working state, and the second working state is referred to as a remote working state.

As mentioned, an insight provided by the present disclosure is to address the aforementioned safety issue when the oxygen supply device is left with the user without an authorized health care provider. Thus, in accordance with the present disclosure, the control unit 210 is configured to determine whether the control signal is authorized before executing one or more control instructions indicated by the control signal received.

In various embodiments, the oxygen supply device is by default set to the remote working state such that the oxygen supply device is controllable only to a remote-control instruction. In that mode, the oxygen supply device is not controllable by anyone locally unless a remote-control signal is received by the control unit 210 to switch the oxygen supply device to the local working state. In this way, when the oxygen supply device is in the remote working state, a non-authorized user would not be able to adjust the oxygen supply device without permission. For example, this can prevent accidental control of the oxygen supply device by someone in the patient's home. As mentioned, nevertheless, the oxygen supply device can be switched to local working state such that a local control is enabled when an authorized switching instruction is transmitted to the oxygen supply device to the control unit 210.

Figure 3:
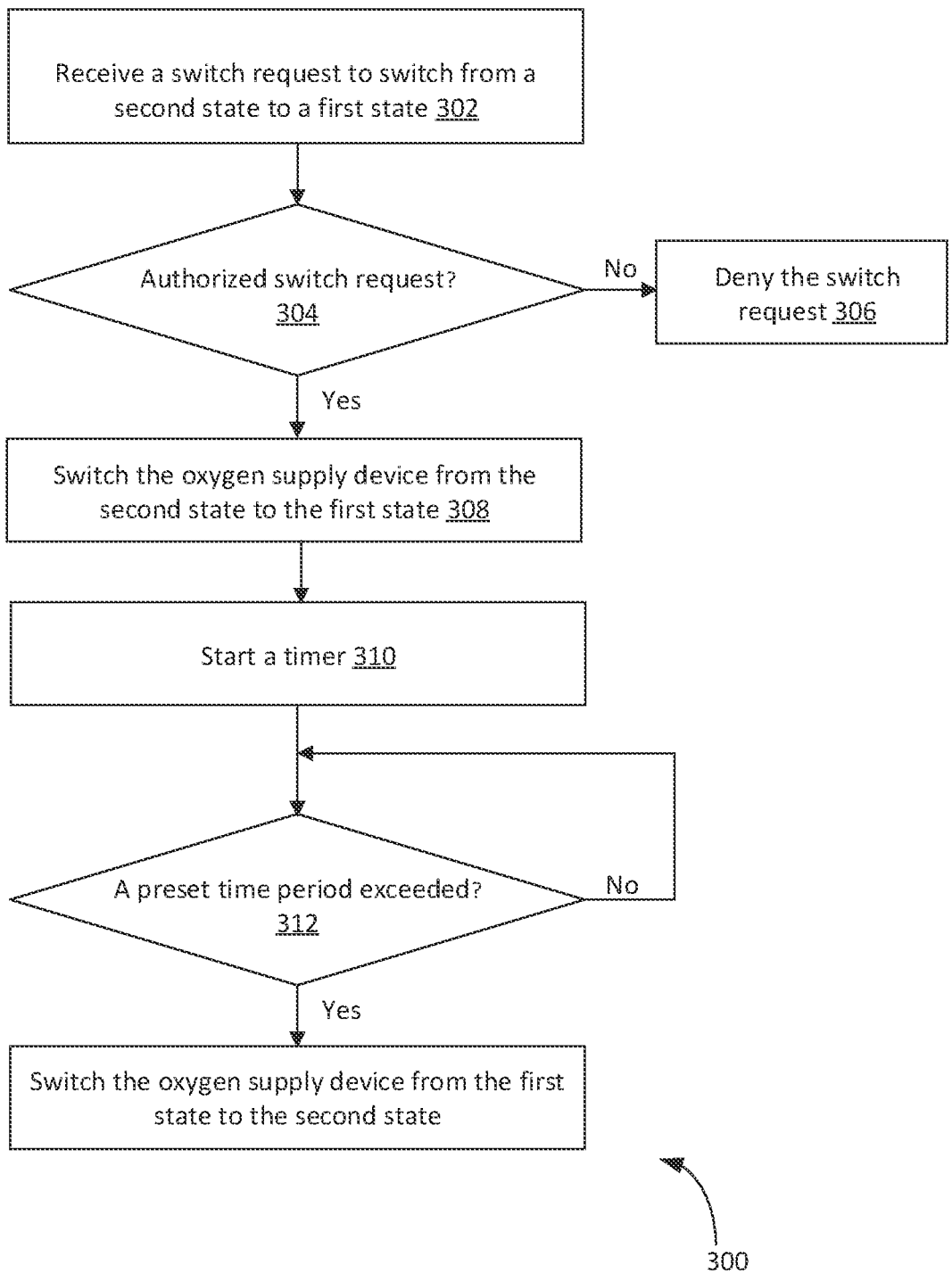
FIG. 3 illustrates one example method that can be implemented by the control unit shown in FIG. 2 in accordance with the present disclosure.

FIG. 3 illustrates one example method 300 that can be implemented by the control unit 210 shown in FIG. 2 in accordance with the present disclosure. The operations of method 300 presented below are intended to be illustrative. In some embodiments, method 300 may be accomplished with one or more additional operations not described and/or without one or more of the operations discussed. Additionally, the order in which the operations of method 300 are illustrated in FIG. 3 and described below is not intended to be limiting.

In some embodiments, method 300 may be implemented in any one of devices 102a and 102n shown in FIG. 1, which may each include one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be designed for execution of one or more of the operations of method 300.

At 302, a switch request is received by oxygen supply device in accordance with the present disclosure. In implementation, the switch request may be carried by a control signal shown in FIG. 2. For example, the switch request may be generated by a health care provider at the computing device 108 shown in FIG. 1 and is transmitted to the oxygen supply device in a form of a control signal. The switch request at 302 is configured to request the oxygen supply device to switch from a second working state (e.g., a remote working state) to a first working state (e.g., a local working state). However, it should be understood that the switch request does not necessarily have to be transmitted remotely.

It is contemplated that the switch request received at 302 can be issued at the oxygen supply device locally. Details of such a switch request will be described later.

At 304, the switch request is examined to determine whether the switch request is authorized. As mentioned, in order to ensure that the oxygen supply device is not controlled by an unauthorized user in locally, the switch request should be issued by an authorized health care provider or controller remotely. Thus, the oxygen supply device, when receive the switch request, should determine whether the request is from an authorized source.

In implementation, various ways may be employed to enable the oxygen supply device to make such a determination. For example, an encryption scheme may be used such that the switch request is encrypted using a key and is only decrypt-able by the oxygen supply device. Another way is that the request may embed various information about the health care provider that issued that switch request, for example biometric information of the health care provider. In that way, the oxygen supply device is configured to register authorized user's biometric information locally on the device when setting up the device for the particular patient. Thus, when the biometric information is received, the oxygen supply device can compare the received biometric information with the registered biometric information to determine whether the switch request is authorized. In implementation, a combination of safety measures may be employed by the oxygen supply device. For example, the switch request is encrypted with biometric information. This can help reduce the risk that the switch request being hacked en-route to the oxygen supply device during transmission. Other technologies such as secure socket layer (SSL) or virtual private network (VPN) may be employed to establish a secure link between the oxygen supply device and the computing device 108 shown in FIG. 1.

At 306, in an event that it is determined that the switch request received at 302 is not issued by an authorized user, the switch request is denied by the oxygen supply device, which remains to be in the remote working state such that no local control is allowed.

At 308, in an event that it is determined that the switch request received at 304 is authorized, the switch request is granted and a switch of the oxygen supply device from the remote working state to the local working state is effectuate such that the local control of the oxygen supply device is allowed.

As mentioned, one insight provided by the present disclosure is that in the local working state, there is a risk of the oxygen supply device being misused because it is located remotely to the health care provider. For addressing this, one way is to limit the time period for which the oxygen supply device is in the local working state such that once this time period expires, the oxygen supply device is automatically switched back to the remote working state.

Thus, at 310, a timer is started after the oxygen supply device is switched to the local working state at 308. The timer is let run and checked during a preset time period as shown at 312. The preset time period can be set during a setup of the device—for example at a configuration of the oxygen supply device for the patient before the oxygen supply device is provided to the patient at his/her home. However, this is not necessarily the only case. Another way of setting up this time period through the computing device 108 shown in FIG. 1. For example, the health care provider may be enabled to set a local control timer when issue the request to switch the oxygen supply device to the local working state from the remote working state.

At 314, after preset time period has expired as indicated by the timer started at 310, the oxygen supply device is switch back to the remote working state such that no local control is continued to be allowed. Thus, the oxygen supply device in accordance some embodiments of the present disclosure, such as the one shown in FIG. 2, has a feature of timed local working state to reduce the risk of misuse when the oxygen supply device is controllable in the local working state.

Figure 4:
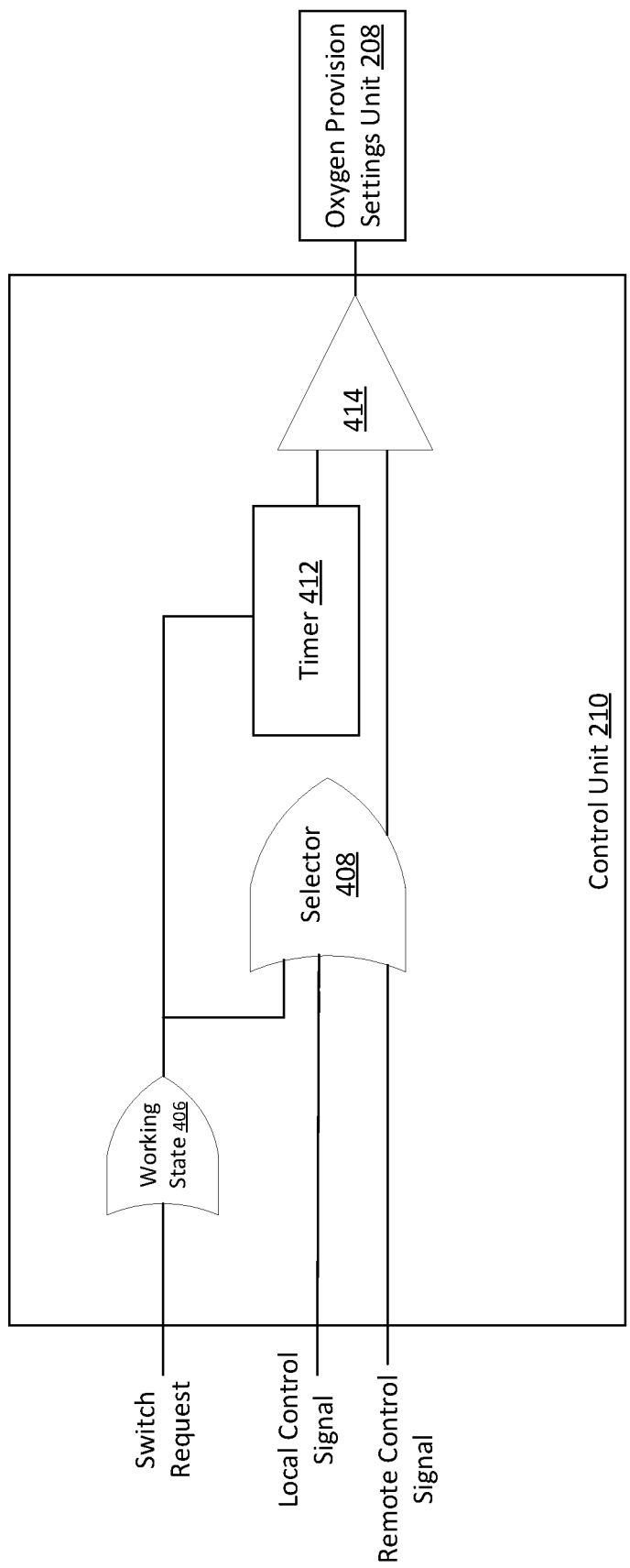
FIG. 4 illustrates one example implementation of the control unit shown in FIG. 2 in accordance with some embodiments.

FIG. 4 illustrates one example implementation of the control unit 210 shown in FIG. 2 in accordance with some embodiments. As can be seen, the control unit 210 in this example implementation is configured to receive at least three inputs: switch request, local control signal, and remote-control signal. These signals are referred to collectively as control signals in FIG. 2. The local control signal is referred to a signal issued locally by a user through the oxygen supply device directly to adjust one or more settings of the oxygen supply device. For example, the oxygen supply device in accordance with the present disclosure may include a knob for switching an oxygen flow rate. In that example, the local control signal is generated when the knob is adjusted from a current flow rate to a new rate. The remote-control signal is referred to as a signal issued remotely by a user to adjust one or more settings of oxygen supply device. For example, in accordance with the present disclosure, the computing device 108 shown in FIG. 1 can provide an interface to enable the health care provider to adjust one or more settings of the oxygen supply device remotely through the computing device.

As mentioned, the switch request is received by the oxygen supply device to switch a working state 406 of the oxygen supply device, which includes a local working state and a remote working state. In this implementation, logic or circuit configured to determine that the switch request is from an authorized user is not shown. In implementation, such logic or circuit may also be included in the control unit of the oxygen supply device shown in FIG. 4. As can be seen, the current working state, local control signal and remote-control signal are fed into a selector 408 for determining which control signal (local or remote) may be used to control the control unit 208. A few different scenarios are described below to illustrate the selector 408.

In a first scenario, the working state of the oxygen supply device is remote working state. In this scenario, the selector ignores the local control signal and only selects the remote-control signal based on the remote working state being the current working state of the oxygen supply device.

In a second scenario, the current working state is local working state. In this scenario, the selector 408 may or may not ignore the remote-control signal. In one design, the selector 408 may be configured to ignore the remote-control signal and only accepts the local control signal. In another design, the selector may be configured to accept both the local and remote-control signals when the current working state is remote working state. In this design, additional logic or circuit may be implemented to address a conflict situation where the local and remote-control signals are received at the same or substantially the similar time and that they are not identical. The logic or circuit may be implemented to determine which signal should be accepted (over the other control signal) in that situation. One implementation is through an override instruction issued by the health care provider when issuing the switch request. For example, the override instruction can specify that the remote-control signal should override the local control signal when the aforementioned situation occurs.

As shown, the timer 412 is configured to be started by the working state 406 when there is a switch from the remote working state to local working state. As mentioned, the timer 412 can be set to a predetermined time-period for which the timer will run. Once the timer 412 expires, it is configured to switch the working stating back to the remote working state as mentioned. As also shown, the control signal selected by the selector 408 is compared with the timer 412 to see if it the control signal is valid. In local working state, this provides a measure to guard the local control signal (selected by the selector 408) to take effect after the timer has expired.

Figure 5:
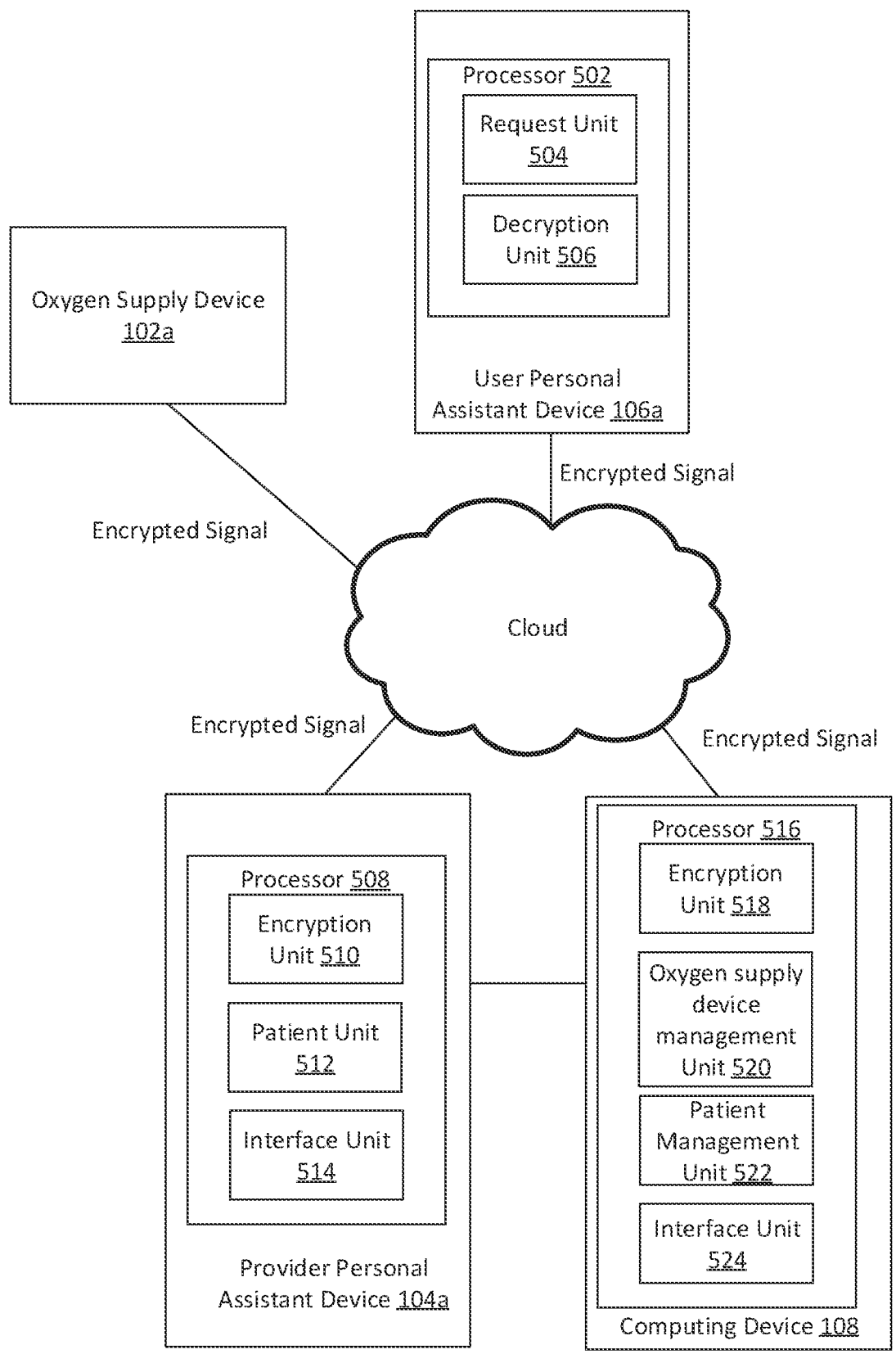
FIG. 5 illustrates an example implementation PDAs, and a computing device shown in FIG. 1 in accordance with some embodiments.

FIG. 5 illustrates an example implementation a PDA 106a, a PDA 104a, and a computing device 108 in accordance with some embodiments. Attention is first directed to the example of the computing device 108 shown in FIG. 5. In this example, the computing device 108 includes a processors configured to execute program components including an encryption unit 518, an oxygen supply device management unit 520, a patient management unit 522, an interface unit 524, and/or any other program components.

The encryption unit 518 is configured to encrypt a signal transmitted onto the cloud, such as switch request signal, and an oxygen supply device control signal shown in FIG. 2. As mentioned, for reducing a risk of communication from the computing device 108 to the oxygen supply device such as oxygen supply device 102a being hacked by a malicious entity, communications with the oxygen supply device is encrypted by the encryption unit 518 in this example. Various encryption methods such as the ones mentioned above may be used by the encryption unit 518 to encrypt the signals from the computing device 108.

The oxygen supply device management unit 520 is configured to manage multiple oxygen supply devices associated with the computing device 108. For example, not intended to be limiting, the computing device 108 is provided by a hospital, which assigns patients oxygen supply devices for use at patients' homes. In that example, the individual oxygen supply devices is managed by the oxygen supply device management unit 520. For instance, the oxygen supply device management unit 520 is configured to manage records of the oxygen supply devices in association with the patients in a following example format:

| ID of computing device 108 | ID of oxygen supply device | Current Working State of the oxygen supply device | Patient's ID | Authorized Users of the oxygen supply device |
| --- | --- | --- | --- | --- |

The ID of the computing device is used to identify a particular computing device 108. For example, the hospital may provide multiple of computing device 108. In that example, an individual computing device 108 can be configured to manage a set of oxygen supply devices. The individual computing devices 108 in that example have a unique ID amongst themselves.

The ID of the oxygen supply device indicates a particular oxygen supply device managed by the computing device 108, such as the oxygen supply device 102a shown in FIG. 1. As mentioned, the computing device 108 can be configured to manage more than one oxygen supply device. Individual oxygen supply devices can have unique IDs to distinguish each other. This can allow the computing device to issue requests or control instructions addressed to a specific oxygen supply device.

The current working state of the oxygen supply device can indicate whether the oxygen supply device is in a local working state or remote working state. In various embodiments, the current working state of the oxygen supply device can also be used to record current settings of the oxygen supply device, such as current oxygen flow rate, purity, provision cycle time, and/or any other settings of the oxygen supply device.

The ID of the patient field can indicate a particular patient associated with the oxygen supply device indicated by the ID of the oxygen supply device filed mentioned above. As mentioned, a particular oxygen supply device can be assigned to a corresponding patient during a period when the patient is under a treatment. This oxygen supply device can be taken by the patient for use at his/her home. The computing device 108 can be configured to manage multiple of such oxygen supply devices assigned to corresponding patients at a given point of time. That is, the computing device 108 via the oxygen supply device management unit 520 can obtain a current working state of the oxygen supply device assigned to a particular patient in this example.

The authorized users field indicate one or more authorized users permitted to change a setting of the oxygen supply device. As mentioned, an individual oxygen supply device may be remotely controlled by a health care provider such as a nurse, a doctor, or a respiration therapist. In some embodiments, a set of users are authorized to control the oxygen supply device as determined at a configuration time of the oxygen supply device, for example when the oxygen supply device is assigned to the patient. For instance, the nurse(s), doctor(s), and the respiration therapist(s) assigned to the patient may be registered as authorized users for the oxygen supply device and their information can be recorded in this field. The recorded information can include their credentials such as username and password at computing device 108 and/or their biometric information such as finger print information. It should be understood that this is not necessarily the only way. In some embodiments, authorized user information for the oxygen supply device may be updated from time to time when the oxygen supply device is assigned to the patient. For example, nurses may have shifts to care for the patient. Authorized user information in that example may be updated on a nurse shift basis to reflect the current nurse(s) on the shift that are authorized to control the oxygen supply device assigned to the patient. In that example, one nurse that may be in the authorized user information when she or he is on a shift to care for the patient and may be off the authorized user information when she or he is off the shift.

The patient management unit 522 is configured to manage one or more patients in treatment with the oxygen supply devices managed by the oxygen supply device management unit 520. For example, for an individual patient, the patient management unit 522 can be configured to keep track of one or more vital signs of this patient (such as his/her breathing rate). The patient management unit 522 can be used to provide patient's information at a given point of time. Information about a particular patient that can be managed by the oxygen supply device management unit patient management unit 522 can include patient's biographical information, location information, biometric information, oxygen supply device usage information by the patient, and/or any other information.

The interface unit 524 is configured to provide an interface to enable a user of the computing device 108, such as a health provider, to interact with the oxygen supply device. Example interface provided by the interface unit 524 can include one or more graphical controls (such as buttons) to allow the health provider to select a particular oxygen supply device, call up patient's vital sign to be displayed in the interface, issue one or more control instructions and/or switch request to the oxygen supply device. The example interface can also provide one or more alerts to the health provider to inform the health provider of certain conditions or threshold situation about the patient. Other ways of implementing the interface provided by the interface unit 524 are contemplated.

Attention is now directed to the PDA 104a shown in FIG. 5. As mentioned, the PDA 104a can be associated with the health provider. An example of the PDA 104a is a smart phone or portable computer associated with the health provider. As can be seen, the PDA 104a in this example includes a processor 508 configured to execute program components including an encryption unit 510, a patient unit 512, an interface unit 514, and/or any other program components.

The encryption unit 510, like the encryption unit 518, is configured to encrypt communications between the PDA 104a and the computing device 108, the PDA 104a and the PDA 106a, and the PDA 104a and the oxygen supply device 102a, and/or any other communications involving the PDA 104a.

The patient unit 512 is configured to manage a patient assigned to the health provider. For example, the patient unit 512 can be configured to obtain one or more vital signs about the patient from the oxygen supply device 102a and/or from the PDA 106a associated with the patient. In implementation, the health provider may be assigned to more than one patient, and the patient unit 512 can be configured to manage multiple patients for the health provider. In some implementations, the patient unit 512 is configured to receive a request from the PDA 106a associated with the patient. The request may ask the health provider to make an adjustment to the oxygen supply device 102a. In that example, after receiving the request through the patient unit 512, the health provider can issue a control instruction to effectuate the requested adjustment on the oxygen supply device 102a for example through the interface provided by the interface unit 524 on the computing device 108.

The interface unit 514 is configured to provide an interface on the PDA 104a. An example interface provided by the interface unit interface unit 514 can include display of information regarding one or more patients assigned to the health provider. For example, through the interface provided by the interface unit 514, the health provider can call up a particular patient assigned to him/her to check the patient's vital signs. As mentioned, this can help the health provider to determine whether adjustment of the oxygen supply device 102a is needed. Another type information presented by the interface provided by the interface unit 514 is alerts which may include an alert about a patient's vital signs indicate a threshold condition has been triggered for the patient. As mentioned, one insight provided by the present disclosure is that the health provider such as nurse does not need to physically check patient's condition on routine visits to patient. The PDA 104a is configured to alert the nurse, for example, the patient is experiencing a breathing difficulty. In response to such an alert, the nurse can call up the patient's vital signs on the PDA 104a to determine if an adjustment of the oxygen supply device 102a is needed to address the breathing difficulty experienced by the patient. In various embodiments, an input device such as a keyboard, a mouse, or a touch screen, or the combination of those three may be employed by the healthcare worker to select an oxygen device, to make a state change of an oxygen device, or to change a configuration setting.

In various implementations, physiological parameters such as oxygen saturation level (SpO2), breathing rate, heart rate and/or any other physiological parameters regarding a patient using the oxygen supply device 102a are received by the computing device 108 periodically or from time to time, from the oxygen supply device 102a. In those implementations, these physiological parameters are managed by the patient management unit 522 as mentioned above. In those implementations, one or more threshold values regarding one or more physiological parameters regarding the patient can be preset such that when values of the one or more physiological parameters breach the preset threshold values, an alert is generated on an interface of the PDA 104a associated with the healthcare worker. For example, as illustration, a preset threshold value of a breathing rate of the patient can be preset such that when the breathing rate of the patient as received from the oxygen supply device 102a from time to time falls below this preset value, an alert is generated on the interface of the PDA 104a to alert the health care worker. The health care worker can then access other physiological parameters of the patient through the interface on the PDA 104a to assess a current condition of the patient. Based on the assessment, the interface on the PDA 104a can be used to facilitate the health care worker to control the oxygen supply device 102a—for example increase an oxygen output level to help the patient until the breathing rate of the patient improves.

In some implementations, one or more images/videos of the patient and/or the surroundings of the oxygen supply device 102a can be transmitted from the oxygen supply device 102a to the computing device 108 from time to time. In those implementations, the oxygen supply device 102a is equipped with cameras to take the image(s) and/or video(s) at a given point of time. In those implementations, the video(s) and/or image(s) regarding the patient are managed by the patient management unit 522. When an alert about the patient is generated on the interface of the PDA 104a, the health care worker is facilitated, in those implementations, to obtain the video(s) and/or image(s) of the patient through the interface on the PDA 104a. This can help the health care work to perform the aforementioned assessment of the patient's condition.

Another alert that can be provided to the health care provider is a request from the patient or someone around the patient remote to the health provider. The request may ask for the health provider to switch the oxygen supply device 102a to the local working state. For example, the patient may be visited by a doctor at his/her home, and the doctor may request a control of the oxygen supply device 102a locally. Such a request can be received by the PDA 104a and presented to the health care provider. In this way, the health care provider can determine whether the oxygen supply device 102a may be switch to the local working state to facilitate a local control of the oxygen supply device 102a.

Attention is now directed to the PDA 106a shown in FIG. 5. The PDA 106a is associated with a patient in this example. For example, the PDA 106a may be a smart device such as a smart phone or a portable computer associated with the patient. However, it is contemplated that in some situations, the PDA 106a may be simply a specific device configured to enable the patient to easily make a request to the health care provider. For example, the PDA 106a may be a device including a call button such that when the patient pushes the call button a request is generated and communicated to the PDA 104a of the health care provider.

As shown, in this example, the PDA 106a includes a processor 502 configured to execute program components including a request unit 504, a decryption unit 506, and/or any other program components. The request unit 504 is configured to generate a request for the patient. The request generated by the request unit 504 may include information indicating an identification of the patient. For example, such information may include biometric information such as fingerprint information of the patient. In implementation, this can be achieved by a fingerprint sensor being installed on the PDA 104a. The identification information of the patient can be used to identify the patient when the request is received, for example, by the PDA 104a. The identification information of the patient can be used to determine whether the patient is authorized to make a request for a particular action to be taken by the health care provider. For example, the patient may be permitted to make a request to have health care provider adjust the oxygen supply device 102a, but not permitted request the health care provider to switch the oxygen supply device 102a to the local working state so that the oxygen supply device 102a can be controlled locally. As another example, the patient may be authorized to request a change to the oxygen supply device 102a including its working state.

The decryption unit 506 is configured to decrypt signals received by the PDA 106a. For example, the PDA 106a may receive a signal from the computing device requesting the PDA 106a to provide vital signs about the patient. In that example, the signal is encrypted by the computing device 108 so that the PDA 106a can determine that such a request is from a legitimate source. Other examples are contemplated.

In some embodiments, the PDA 106a is a device including at least control mechanism enabling the patient to make a request to adjust a comfort setting of the oxygen supply device 102a. For example, in one embodiment the PDA 106a is configured with two large button to enable the patient to increase and decrease a temperature of the oxygen supplied by the oxygen supply device 102a. For instance, one of the buttons has a sign of an up arrow and the other button has a sign of a down arrow button. A pressing of the up-arrow button can cause a signal to be generated by the PDA 106a to request an increase of a temperature of the oxygen supplied by the oxygen supply device 102a. This request can then be transmitted by the PDA 106a over the network to the computing device 108. After receiving the request, the computing device 108 is configured to generate a corresponding instruction to instruct the oxygen supply device 102a to increase the temperature of the oxygen supplied to the patient. The corresponding instruction is then transmitted by the computing device 108 over the network to the oxygen supply device 102a for execution. A mechanism for facilitating decreasing of the temperature of oxygen supplied by the oxygen supply device 102a can be similarly implemented and is not repeated.

In various embodiments, the computing device is configured to control the adjustment of the temperature of oxygen supplied to the patient is between 31 and 37 Celsius. However, other temperature range is also contemplated. In those embodiments, after receiving a request to increase or decrease a temperature of oxygen supplied to the patient, the computing device 108 is configured to check if the request is to cause the temperature of the oxygen supplied to the patient will be outside this temperature range. If it is determined the request will cause the temperature to be outside this range, the computing device 108, in those embodiments, is configured to cap or floor the temperature adjust to 37 or 31 Celsius.

Figure 6:
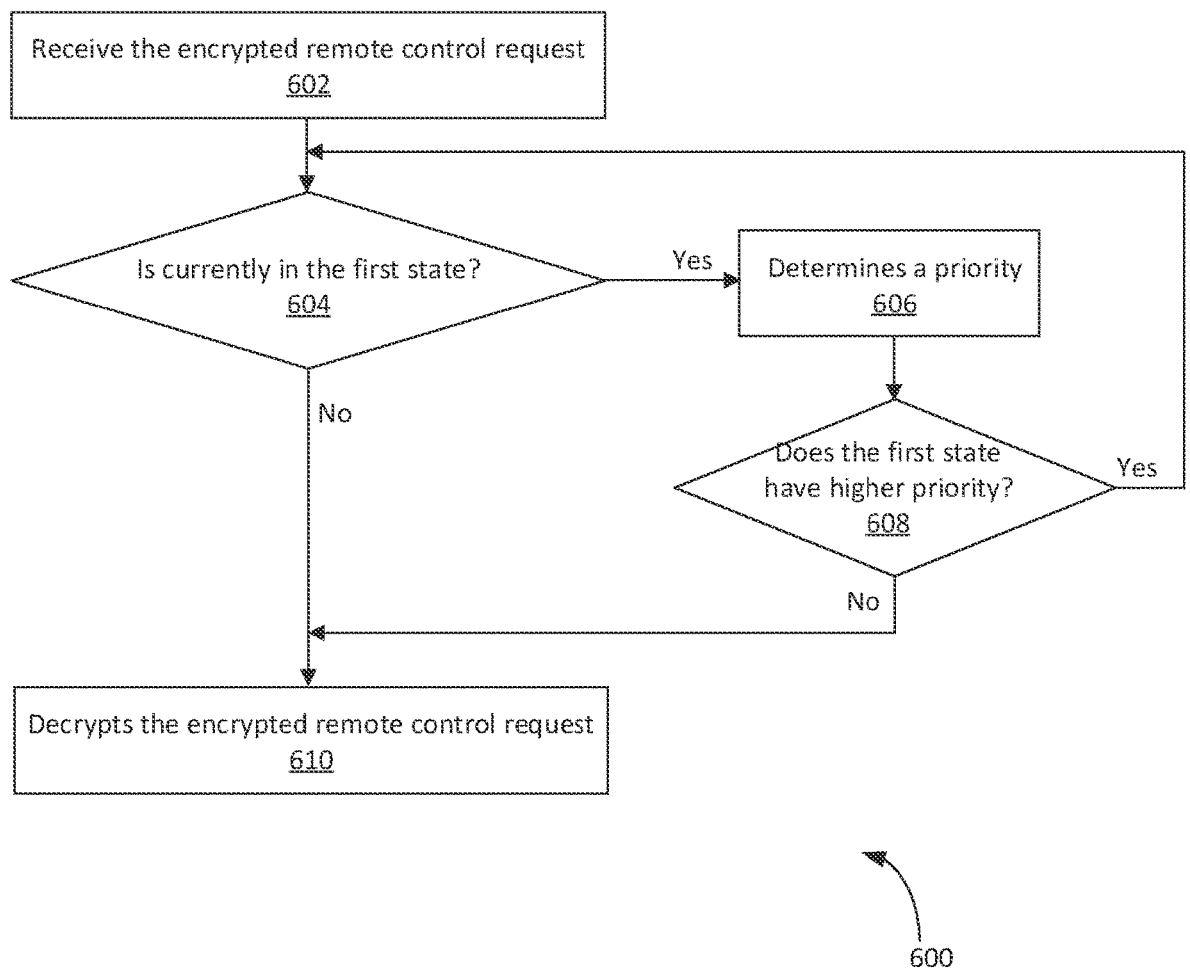
FIG. 6 illustrates an example method of controlling an oxygen supply device in accordance with some embodiments.

Attention is now directed to FIG. 6, where an example method 600 of controlling the oxygen supply device is described in accordance with some embodiments. The operations of method 600 presented below are intended to be illustrative. In some embodiments, method 600 may be accomplished with one or more additional operations not described and/or without one or more of the operations discussed. Additionally, the order in which the operations of method 600 are illustrated in FIG. 6 and described below is not intended to be limiting.

In some embodiments, method 600 may be implemented in any one of devices 102a and 102n shown in FIG. 1, which may each include one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be designed for execution of one or more of the operations of method 600.

At 602, a remote-control request is received at the oxygen supply device in accordance with the present disclosure. The remote-control request received at 602 may be switch request to switch a working state of the oxygen supply device, a request to control one or more settings of the oxygen supply device, and/or any other types of requests. It should be noted the request received at 602 is encrypted and may be issued by a remote computing device such as computing device 108 shown in FIG. 1. In implementation, operation at 602 may be implemented by a control unit the same as or substantially similar to the control unit 210 described and illustrated herein.

At 604, a current working state of the oxygen supply device is checked to determine if the oxygen supply device is in a first working state, e.g., a local working state. In this example method, logic is provided when there is a situation a remote-control request is transmitted to the oxygen supply device to make a change to the oxygen supply device. In that situation, the oxygen supply device may not be desired to be controlled remotely. If that's preference, the oxygen supply device can be configured to ignore the remote-control request. However, there also could be a situation where it is desired to accept the remote-control request when the oxygen supply device is in the local working state. For example, local control may be granted so that the oxygen supply device is controllable by someone at patient's site. However, in that situation, the oxygen supply device may still be controlled remotely if the health care provider determines to override the changes made locally at the patient's site. For instance, this may happen if the health care provider determines a mistake or misuse is made to the oxygen supply device, or may determine that the patient's condition has changed so new settings are needed.

At 606, a priority of the remote-control request is determined. As mentioned, in some situations, the remote-control request may be ignored while in some situations it may be accepted. The determination at 606 may be based on a current working state and/or a priority assigned to remote-control requests in general. For example, the current working state is local working state and the priority for the remote-control request is override, which means it has a higher priority than the local working state. In that situation, whenever the remote-control request is received, the oxygen supply device's setting is changed according to the remote-control request. In another situation, the current working state is local working state and the priority of the remote-control request is 0, which means whenever the remote-control request is received, the remote-control request will be denied. Still in another situation, the current working state is local working state and the priority of the remote-control request is lower than the local working state but not 0, which means if the remote-control request is not inconsistent with the local working state, it will be accepted. For example, if the remote-control request asks to set an oxygen provision frequency in a period, which has not been set for the period and thus is not inconsistent with the local working state, the remote-control request is granted. However, if the remote-control request asks to change an oxygen flow rate, which is inconsistent with the local working state, the remote-control request will be denied. In implementation, operation at 606 may be implemented by a control unit the same as or substantially similar to the control unit 210 described and illustrated herein.

At 608, a comparison is made to determine if the local working state has a higher priority than the remote-control request. Some example ways of making this determination is described above. At 610, after determining that the remote-control request can be accepted, the remote-control request is decrypted for implementing the request. In implementation, operation at 608 and 610 may be implemented by a control unit the same as or substantially similar to the control unit 210 described and illustrated herein.

Example Computer System

Figure 7:
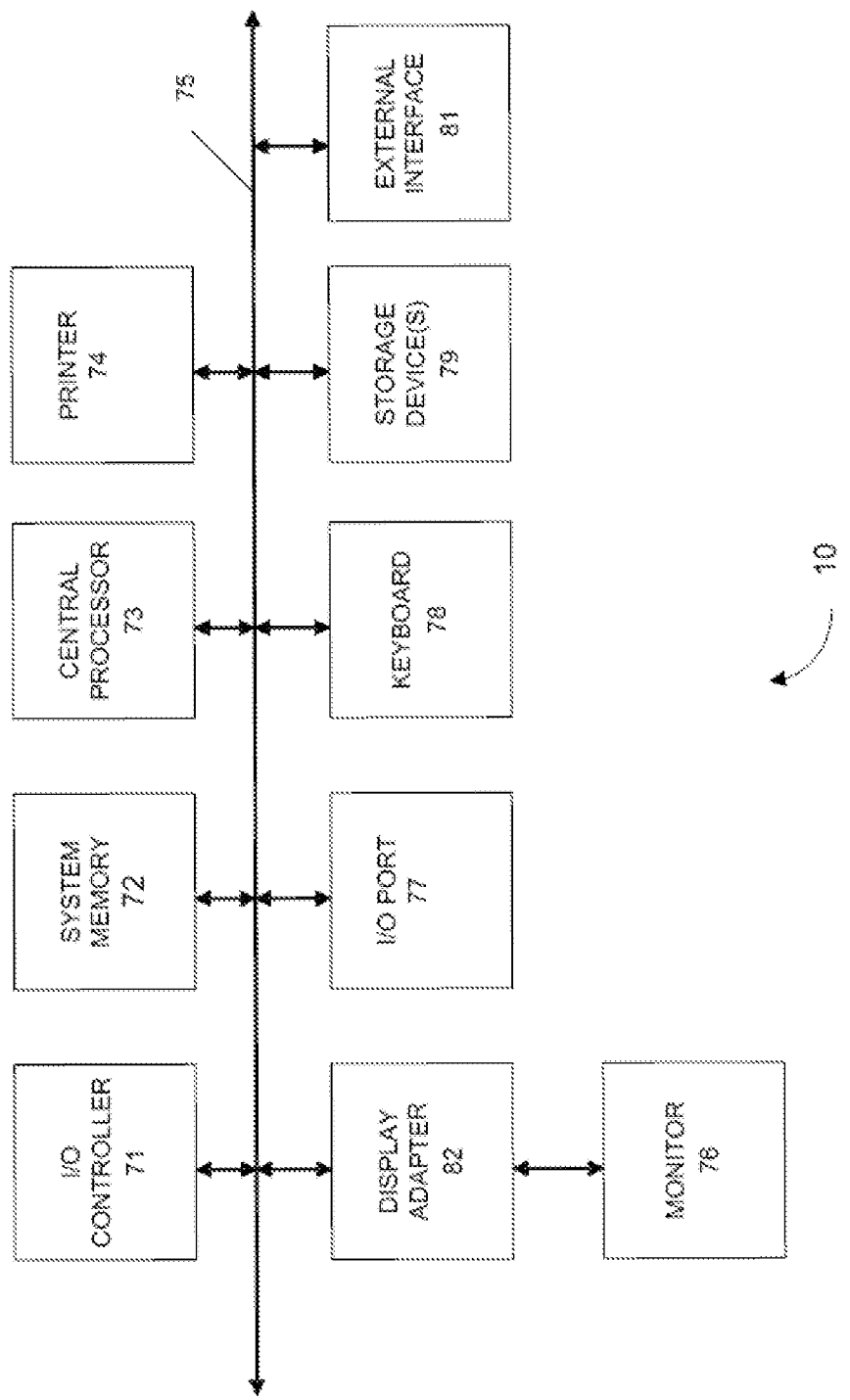
FIG. 7 illustrates an example of a computer system for implementing various embodiments described and illustrated herein.

Any of the computer systems mentioned herein may utilize any suitable number of subsystems. Examples of such subsystems are shown in FIG. 7 in computer system 10, which can be configured to implement various features and/or functions described herein. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 7 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary. The use of "or" is intended to mean an "inclusive or," and not an "exclusive or" unless specifically indicated to the contrary.

Two states are also for illustration purpose. It is possible for an embodiment where remote command and local command for changing oxygen device settings be accepted without state switches.

All patents, patent applications, publications, and descriptions mentioned herein are incorporated by reference in their entirety for all purposes. None is admitted to be prior art.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

What is claimed is:

1. An oxygen supply device having multiple operational states including a first state and a second state, wherein in the second state, the oxygen supply device is controllable only to a remote-control instruction, and in the first state, the oxygen supply device is controllable to a local control instruction, the oxygen supply device comprising a circuit configured to perform:
   receiving a switch request requesting to switch the oxygen supply device from the second state to the first state;
   determining whether the switch request is authorized to effectuate the switch;
   in response to a determination that the switch request is authorized to effectuate the switch, switching the oxygen supply device from the second state to the first state and starting a timer; and
   determining that the timer has exceeded a preset time period and switching the oxygen supply device from the first state to the second state.

2. The oxygen supply device of claim 1, wherein the signal requesting the switch is received over an electronic communication channel from a remote computing device, and wherein the signal includes information indicating that the remote computing device has authorized the switch.

3. The oxygen supply device of claim 1, wherein the oxygen supply device comprises an element configured to receive the request to switch from the user and the signal requesting the switch is received, wherein the element is further configured to obtain biometric information of the user, and wherein the determination whether the signal is authorized to effectuate the switch is based on the biometric information of the user.

4. The oxygen supply device of claim 1, wherein the oxygen supply device comprises an identification in association with one or more users authorized to control the oxygen supply device, wherein the determination whether the signal is authorized to effectuate the switch comprises determining whether the signal is from the one of the one or more users authorized to control the oxygen supply device.

5. The oxygen supply device of claim 1, wherein the oxygen supply device is not controllable by the remote-control instruction in the first state.

6. The oxygen supply device of claim 1, wherein the oxygen supply device is controllable by the remote-control instruction in the first state.

7. The oxygen supply device of claim 1, wherein the oxygen supply device includes a high flow nasal cannula device.

8. The oxygen supply device of claim 1, wherein the circuit of the oxygen supply device is configured to receive an instruction initiated by a user to change a temperature of the oxygen supplied by the oxygen supply device.

9. A method to facilitate remote-controlling an oxygen supply device having multiple operational states including a first state and a second state, wherein in the second state, the oxygen supply device is controllable only to a remote-control instruction, and in the first state, the oxygen supply device is controllable to a local control instruction, wherein the method comprises:
   receiving a switch request requesting to switch the oxygen supply device from the second state to the first state;
   determining whether the switch request is authorized to effectuate the switch;
   in response to a determination that the switch request is authorized to effectuate the switch, switching the oxygen supply device from the second state to the first state and starting a timer; and
   determining that the timer has exceeded a preset time period and switching the oxygen supply device from the first state to the second state.

10. The method of claim 9, wherein the signal requesting the switch is received over an electronic communication channel from a remote computing device, and wherein the signal includes information indicating that the remote computing device has authorized the switch.

11. The method of claim 9, further comprising:
    obtaining biometric information of the user; and, wherein the determination whether the signal is authorized to effectuate the switch is based on the biometric information of the user.

12. The method of claim 9, wherein the oxygen supply device comprises an identification in association with one or more users authorized to control the oxygen supply device and wherein the determination whether the signal is authorized to effectuate the switch comprises determining whether the signal is from the one of the one or more users authorized to control the oxygen supply device.

13. The method of claim 9, wherein the oxygen supply device is not controllable by the remote-control instruction in the first state.

14. The method of claim 9, wherein the oxygen supply device is controllable by the remote-control instruction in the first state.

15. The method of claim 9, wherein the oxygen supply device includes a high flow nasal cannula device.

16. A non-transitory computer medium configured to store computer programs to facilitate remote-controlling an oxygen supply device having multiple operational states including a first state and a second state, wherein in the second state, the oxygen supply device is controllable only to a remote-control instruction, and in the first state, the oxygen supply device is controllable to a local control instruction, wherein the computer programs are executable to cause a processor of a computing device to perform:

receiving a switch request requesting to switch the oxygen supply device from the second state to the first state;

determining whether the switch request is authorized to effectuate the switch;

in response to a determination that the switch request is authorized to effectuate the switch, switching the oxygen supply device from the second state to the first state and starting a timer; and determining that the timer has exceeded a preset time period and switching the oxygen supply device from the first state to the second state.

17. The non-transitory computer medium of claim 16, wherein the signal requesting the switch is received over an electronic communication channel from a remote computing device, and wherein the signal includes information indicating that the remote computing device has authorized the switch.

18. The non-transitory computer medium of claim 16, further comprising:

obtaining biometric information of the user; and, wherein the determination whether the signal is authorized to effectuate the switch is based on the biometric information of the user.

19. The non-transitory computer medium of claim 16, wherein the oxygen supply device comprises an identification in association with one or more users authorized to control the oxygen supply device and wherein the determination whether the signal is authorized to effectuate the switch comprises determining whether the signal is from the one of the one or more users authorized to control the oxygen supply device.

20. The non-transitory computer medium of claim 16, wherein the oxygen supply device is not controllable by the remote-control instruction in the first state.

\* \* \* \* \*